(12) United States Patent
Janssens

(10) Patent No.: US 7,008,381 B2
(45) Date of Patent: Mar. 7, 2006

(54) DEVICE FOR TAKING A TISSUE SAMPLE

(76) Inventor: Jacques Phillibert Janssens, Klein Hilstraat 5, Hasselt (BE) 3500

(*) Notice: Subject to any disclaimer, the term of this patent is extended or adjusted under 35 U.S.C. 154(b) by 187 days.

(21) Appl. No.: 10/258,531

(22) PCT Filed: Feb. 13, 2002

(86) PCT No.: PCT/BE02/00017

§ 371 (c)(1),
(2), (4) Date: Oct. 25, 2002

(87) PCT Pub. No.: WO02/065919

PCT Pub. Date: Aug. 29, 2002

(65) Prior Publication Data

US 2003/0114773 A1   Jun. 19, 2003

(30) Foreign Application Priority Data

Feb. 16, 2001  (BE) .................... 2001/0110

(51) Int. Cl.
*A61B 10/00*   (2006.01)

(52) U.S. Cl. .................................... 600/564
(58) Field of Classification Search ........... 600/562, 600/567, 435, 564, 568; 606/180; 605/116; 604/528, 170.03, 264
See application file for complete search history.

(56) References Cited

U.S. PATENT DOCUMENTS

| 2,850,007 | A | * | 9/1958 | Lingley ................. 600/567 |
| 3,683,891 | A | | 8/1972 | Eskridge et al. |
| 4,682,606 | A | * | 7/1987 | DeCaprio .............. 600/567 |
| 5,018,530 | A | * | 5/1991 | Rank et al. ............ 600/562 |
| 5,221,269 | A | * | 6/1993 | Miller et al. .......... 604/528 |
| 5,417,703 | A | | 5/1995 | Brown et al. |
| 5,488,958 | A | | 2/1996 | Topel et al. |
| 5,762,069 | A | | 6/1998 | Kelleher et al. |
| 6,083,237 | A | | 7/2000 | Huitema et al. |

FOREIGN PATENT DOCUMENTS

| EP | 0481685 | 4/1992 |
| EP | 0943292 | 9/1999 |

* cited by examiner

*Primary Examiner*—Max F. Hindenburg
*Assistant Examiner*—Brian Szmal
(74) *Attorney, Agent, or Firm*—James Creighton Wray; Meera P. Narasimhan

(57) ABSTRACT

Device for taking a tissue sample (34), characterized in that it comprises a spirally shaped tissue-receiving element (2), the outer free extremity of which extents in a direction which is situated in the prolongation of the spiral course of the spirally shaped tissue-receiving element (2), on one hand, and a cutting element (4–38), on the other hand, which can cooperate with the circumference of the spirally shaped tissue-receiving element (2) in order to provide in a cutting function.

22 Claims, 9 Drawing Sheets

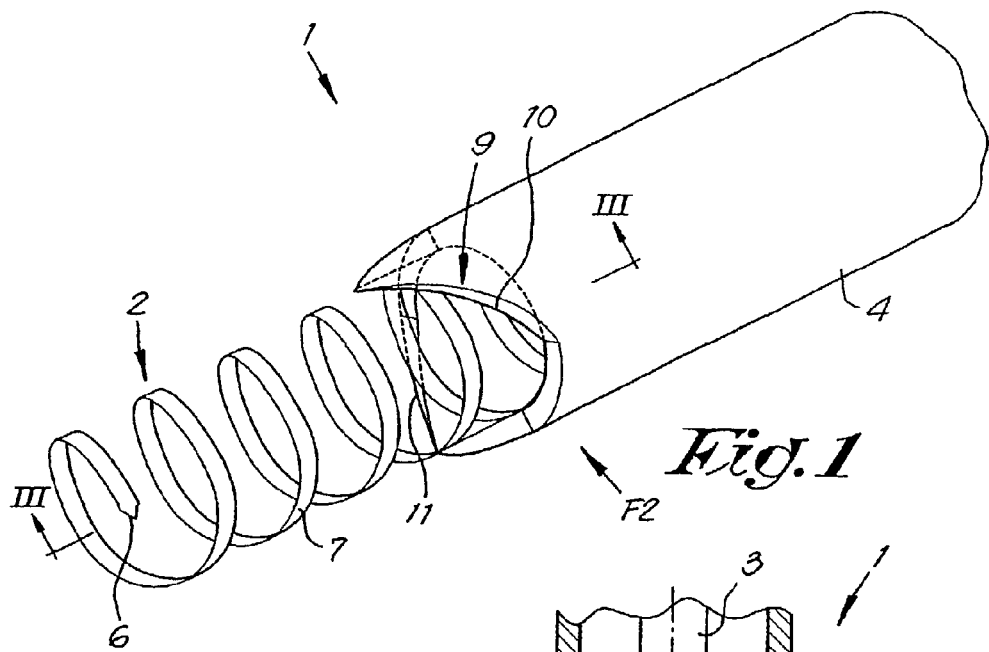
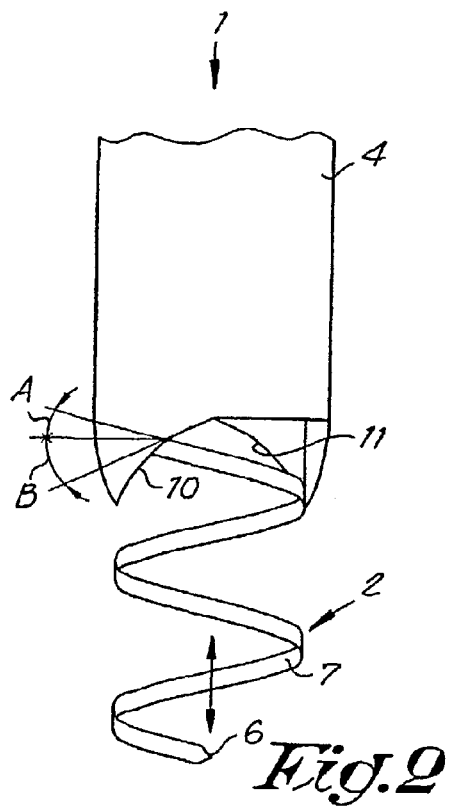
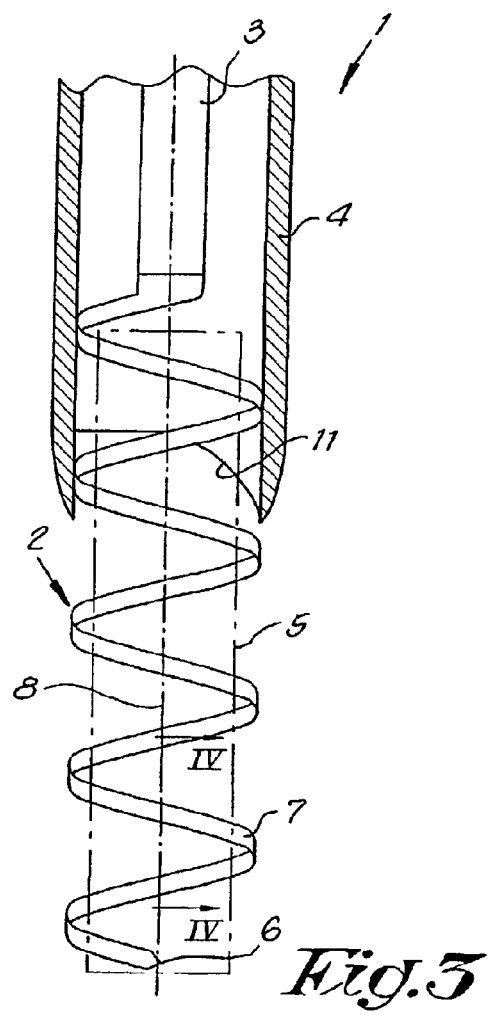
Fig.1
Fig.2
Fig.3

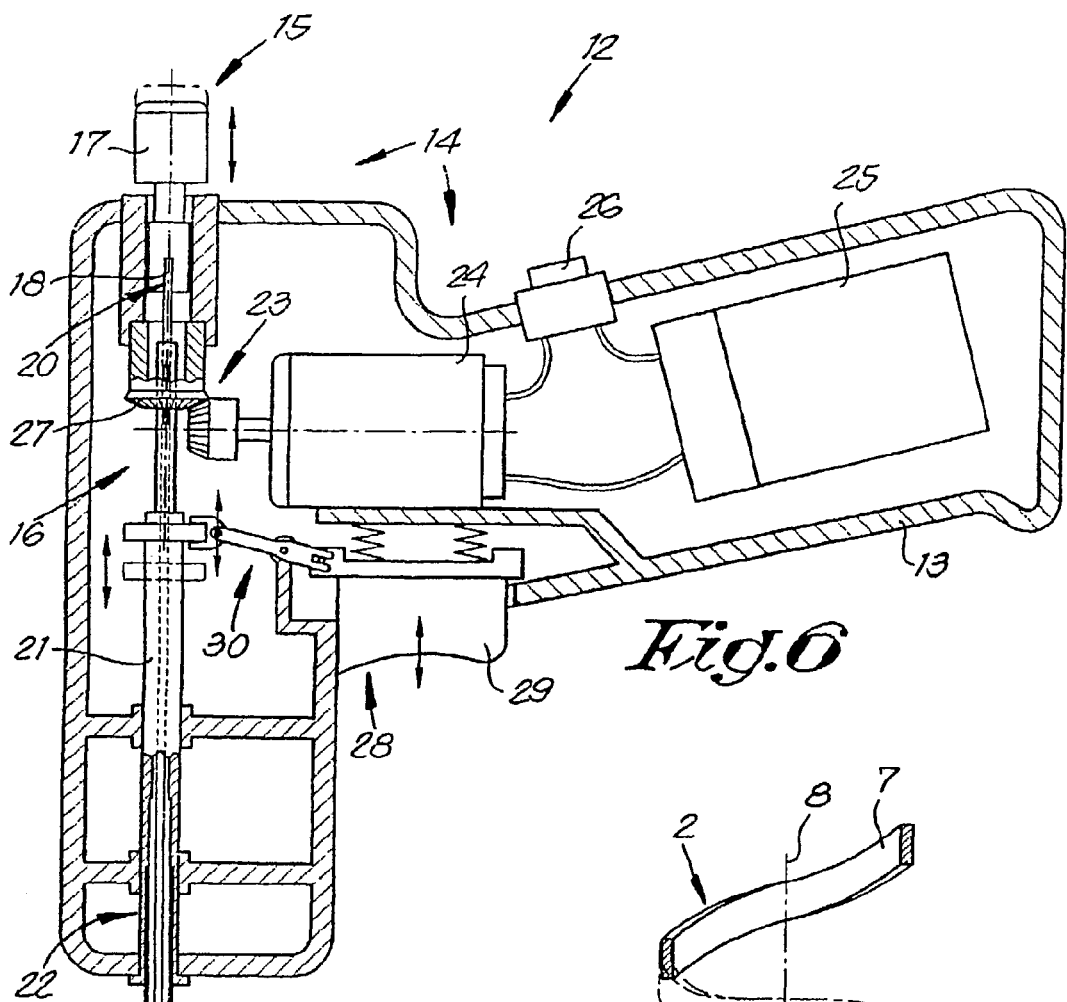
Fig.6
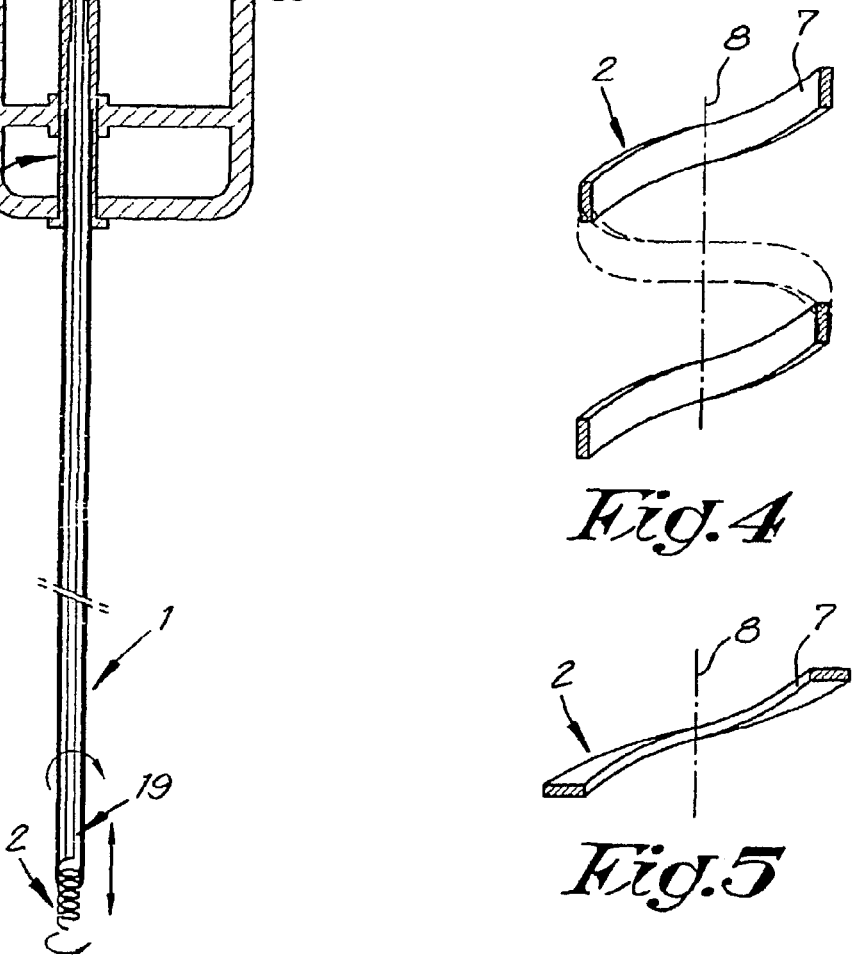
Fig.4
Fig.5

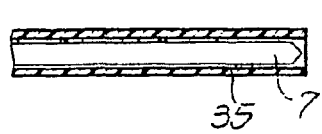
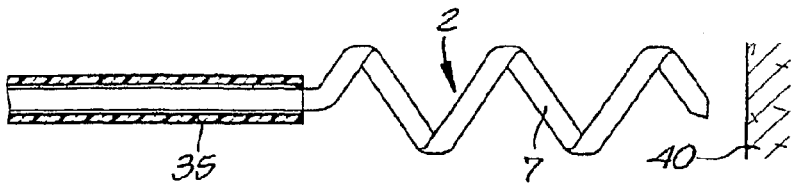
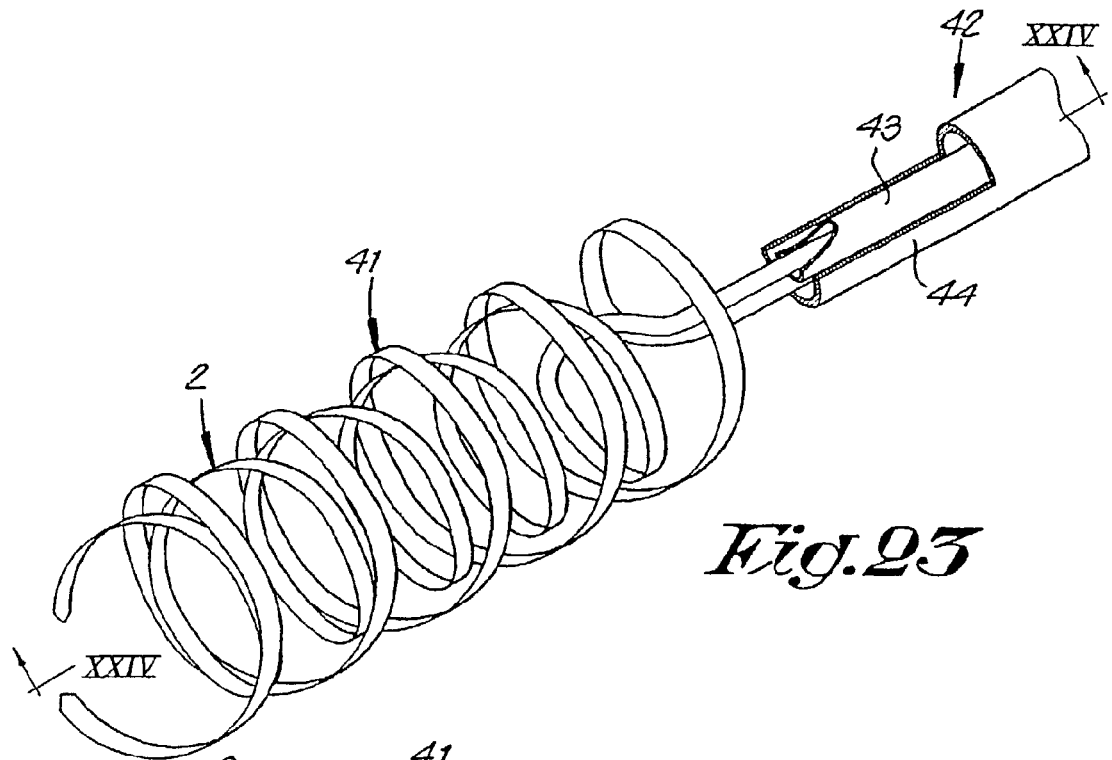
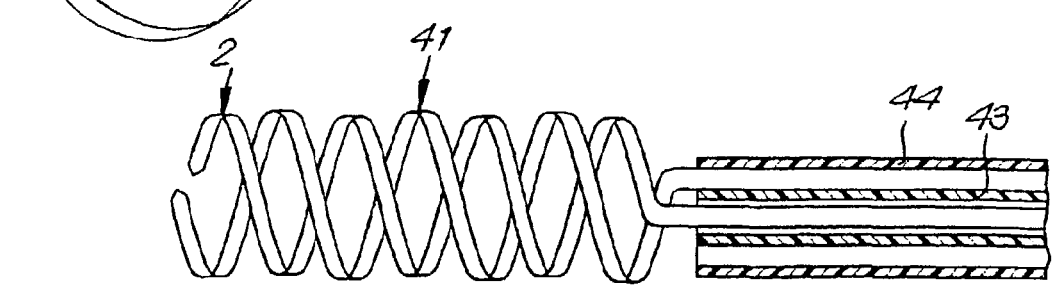

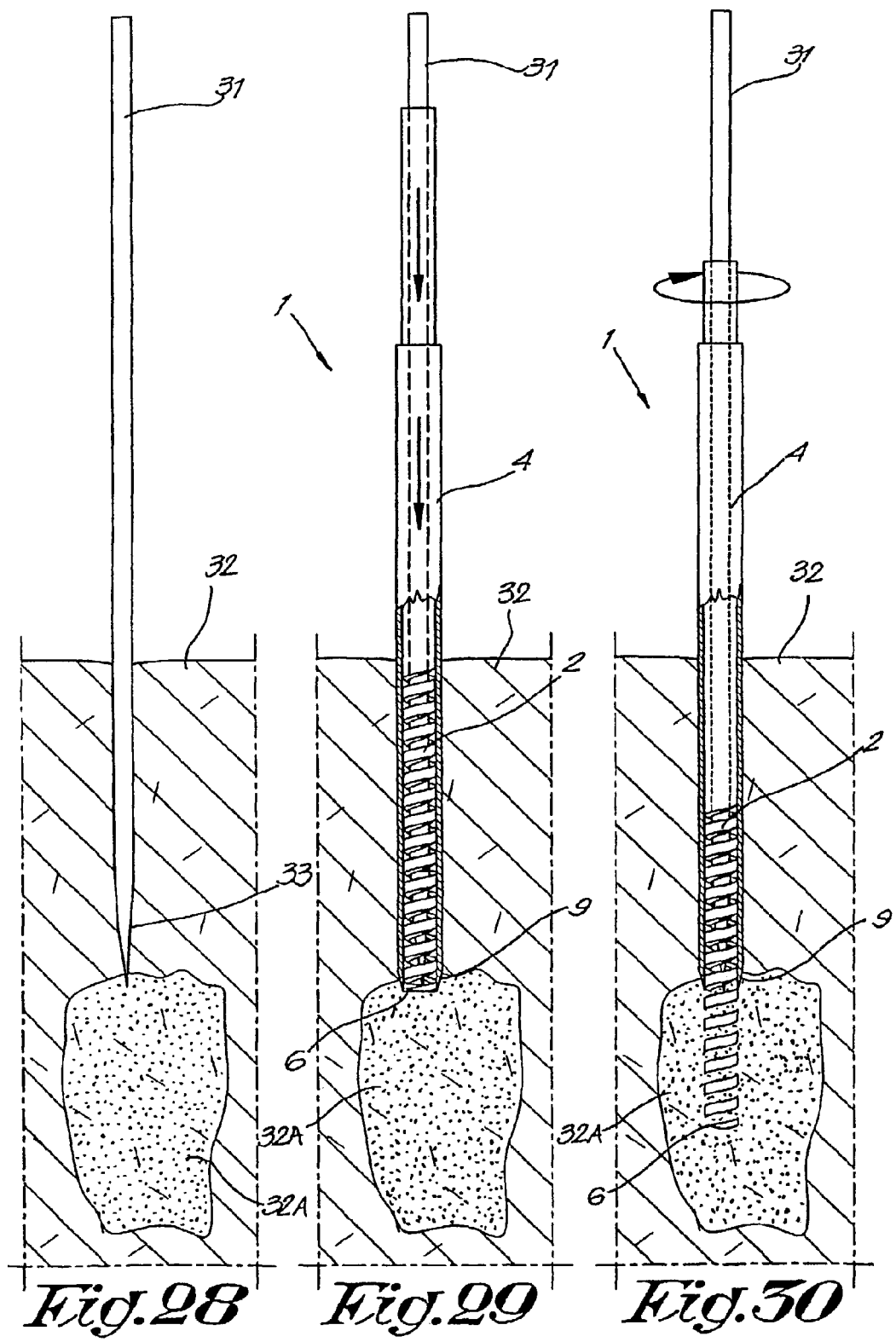

DEVICE FOR TAKING A TISSUE SAMPLE

This application claims the benefit of Belgian Application No. 2001/0110 filed Feb. 16, 2001 and PCT/BE02/00017 filed Feb. 13, 2002.

BACKGROUND OF THE INVENTION

1. Field of the Invention

This invention relates to a device for taking a tissue sample, in other words, to a biopsy device.

2. Discussion of the Related Art

Devices for taking a tissue sample are already known in different forms, amongst others, from the patent document U.S. Pat. No. 6,027,458.

It is also known that such devices for taking tissue samples may provided with a spirally shaped tissue-receiving element. Examples of such devices are disclosed in documents EP 0,481,685, U.S. Pat. No. 3,683,891, U.S. Pat. No. 5,417,703, U.S. Pat. No. 5,488,958, U.S. Pat. No. 5,762,069, and U.S. Pat. No. 6,083,237.

SUMMARY OF THE INVENTION

The invention aims at an improved device for taking a tissue sample, said device being of the type having a spirally shaped tissue-receiving element. More particularly, the invention aims at an improved device, offering the advantage that tissue samples can be taken very efficiently, with a minimum of damages of the sample itself, as well as of the tissue surrounding the sample.

To this aim, the invention in the first place relates to a device for taking a tissue sample, which is characterized in that it comprises a spirally shaped tissue-receiving element, the outer free extremity of which extents in a direction which is situated in the prolongation of the spiral course of the spirally shaped tissue-receiving element, on one hand, and a cutting element, on the other hand, which can cooperate with the circumference of the spirally shaped tissue-receiving element in order to provide in a cutting function.

The spirally shaped tissue-receiving element has as an advantage that it can easily be inserted into the tissue and subsequently a sample can be taken from the tissue in an efficient manner. At the same time, due to the spiral shape of the tissue-receiving element, a good anchoring between the tissue sample and the tissue-receiving element is made possible.

Due to the fact that the free extremity of the spirally shaped tissue-receiving element extends in the prolongation of the course of the spiral, during the screwing-in of the tissue-receiving element into the tissue, the portion of tissue which is located centrally in between the spiral, and which finally is to form the sample, is not touched by the spirally shaped tissue-receiving element and, as a consequence, is not damaged. That the free extremity extends in the prolongation of the spiral, also offers the advantage that the tissue-receiving element can be smoothly inserted in the tissue, only by a screwing force, without the need of creating an axial pushing force. Furthermore, due to the use of a cutting element which cooperates with the circumference of the spirally shaped tissue-receiving element, the portion of tissue caught in the spiral can be separated from the surrounding tissue in a very adequate and precise manner, with no or almost no damage done to the surrounding tissue of the patient.

Preferably, the tissue-receiving element has a helical course, as a consequence of which it can easily be brought into the tissue by means of a screw movement.

Further, the tissue-receiving element preferably shows one or more of the following characteristics:

that this spirally shaped tissue-receiving element surrounds a free axial passage space, with the advantage that the spiral shape is surrounding a central, continuously extending receiving space;

that the spiral of the spirally shaped tissue-receiving element, measured according to a direction perpendicular to the axial direction, has a width which is smaller than one third of the global diameter taken up by the spirally shaped tissue-receiving element;

that this spirally shaped tissue-receiving element extends over several turns, as a consequence of which a good anchoring between the tissue sample to be removed and the tissue-receiving element is obtained, whereby this tissue-receiving element, together with the cylindrical element described in the following, can perform a cutting movement, such that the tissue sample is loosened from the remainder of the tissue;

that this spirally shaped tissue-receiving element shows a sharp point at its free front extremity, as a consequence of which it can easily penetrate into the tissue;

that the aforementioned sharp point extends in a direction which is situated in the prolongation of the spirally shaped course of the spirally shaped tissue-receiving element, as a consequence of which the spirally shaped tissue-receiving element, during turning, automatically keeps a spirally shaped course;

that this spirally shaped tissue-receiving element is formed of a body with a flat cross-section, as a consequence of which, on one hand, an axial guide is offered and, on the other hand, also a good anchoring in a tissue can be realized, as a result of which a relatively large traction force can be exerted on the tissue in order to pull the tissue sample loose;

that this spirally shaped tissue-receiving element is formed of a body having a cross-section which tapers towards the outside, and preferably ends in a tip, resulting in the advantage that there is a minimum of contact with the afterwards remaining tissue;

that this spirally shaped tissue-receiving element is formed by a body showing lateral surfaces having an inclination in respect to the plane perpendicular to the axial direction of the device, which is less than 30 degrees, resulting in the advantage that an optimum anchoring of the sample in the receiving element can be guaranteed.

The device preferably also comprises at least one cylindrical element or "cannula" surrounding the spirally shaped tissue-receiving element. This cylindrical element may be constructed such that it only functions as a guide or sleeve, but preferably it will fulfill the function of the abovementioned cutting element. In such case, this cylindrical element will preferably cooperate with the spirally-shaped tissue-receiving element in such a manner that, due to the turning in mutual respect, a cutting effect is realized. In other words, this means that the spirally shaped tissue-receiving element fits into the cylindrical element. The cylindrical element preferably is rotatable.

According to the invention, the spirally shaped tissue-receiving element can be applied in combination with a biopsy needle as well as in combination with a catheter.

By applying the tissue-receiving element in combination with a catheter, the advantage is obtained that tissue samples can be taken at a large number of places which in the past had been difficult to reach. According to the invention, this combination is not limited to spirally shaped tissue-receiving elements, however, it may also be realized by means of other tissue-receiving elements.

Without regarding whether a spirally shaped tissue-receiving element or a tissue-receiving element of another design, is concerned, it is preferred that the tissue-receiving element is axially shiftable in respect to the catheter-like element, more particularly shiftable between at least two positions, on one hand, a position whereby the tissue-receiving element is situated at least partially out of the most forward extremity of the catheter-like element, and, on the other hand, a position whereby the tissue-receiving element is in a more retracted position in respect to the catheter-like element.

BRIEF DESCRIPTION OF THE DRAWINGS

With the intention of better showing the characteristics of the invention, hereafter, as an example without any limitative character, several preferred forms of embodiment are described, with reference to the accompanying drawings, wherein:

FIG. 1 schematically and in perspective represents a device according to the invention;

FIG. 2 represents a view according to arrow F2 in FIG. 1;

FIG. 3 represents a cross-section according to line III—III in FIG. 1;

FIG. 4 represents a cross-section according to line IV—IV in FIG. 3;

FIG. 5 represents a view analogous to that of FIG. 4, however, for a variant;

FIG. 6 schematically and in cross-section represents an apparatus for taking a tissue sample by means of the device according to the invention;

FIGS. 7 to 16 represent in various steps how a tissue sample can be taken by means of a device according to the invention, wherein FIGS. 8, 10 and 12 are cross-sections at a larger scale, according to lines VIII—VIII, X—X and XII—XII in FIGS. 7, 9 and 11, respectively;

FIGS. 20 to 22 schematically represent another variant in different conditions;

FIG. 23 represents another device according to the invention;

FIG. 24 represents a cross-section according to line XXIV—XXIV in FIG. 23;

FIGS. 28 to 32 represent in various steps how a tissue sample can be taken by means of a device which, for example, comprises elements of the construction shown in FIGS. 25 and 26.

DETAILED DESCRIPTION OF THE PREFERRED EMBODIMENTS

Figure 7:
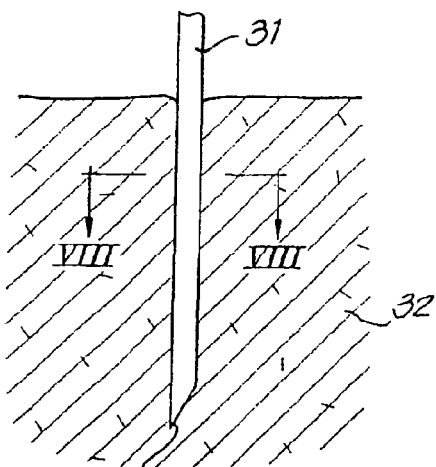

As represented in FIGS. 1 to 3, the invention relates to a device 1 for taking a tissue sample, with the particularity that it comprises a spirally shaped tissue-receiving element 2.

This tissue-receiving element 2 is situated at the extremity of an oblong portion, in the represented example a bar- or wire-shaped portion 3, with which the spirally shaped tissue-receiving element 2 can be manipulated. According to a variant, this, for example, also may be a tube-shaped portion. Apart therefrom, the device 1, as represented, also comprises a cutting element, preferably a cylindrical element 4, which can surround the spirally shaped tissue-receiving element 2.

As can be seen in the embodiment of FIGS. 1 to 3, the spirally shaped tissue-receiving element 2 has a helical course.

The spirally shaped tissue-receiving element 2 is made such that it surrounds a free axial passage space, in other words, there is a free, axially extending space 5 between the turns of this element, the contour of which space is indicated in dash-dotted line in FIG. 3.

The spirally shaped tissue-receiving element 2 extends over several turns, preferably at least two, however, even better, more than two, as is clearly visible in FIGS. 1 to 3.

At the distal end, the spirally shaped tissue-receiving element 2 shows a free extremity which extends in a direction which is situated in the prolongation of the spirally shaped course of the tissue-receiving element 2. In other words, the free extremity is completely, or at least substantially, located within the cylindrical mantle followed by the helicoidal spiral and, contrary to the devices disclosed in several of the above-mentioned prior art documents, does not end up in the axial axis of the device. Moreover, the free extremity is preferably provided with a sharp point 6 which is also directed according to the helicoidal course followed by said spiral.

The spirally shaped tissue-receiving element 2 as such preferably is formed of a body 7 with a flat and/or square and/or trapezoid and/or rectangular cross-section.

In the case of a rectangular cross-section, the body 7 can extend with its longitudinal direction parallel to the longitudinal axis 8 of the spirally shaped tissue-receiving element 2, as represented in FIG. 4, as well as, according to a variant, extend with its longitudinal direction perpendicular to the longitudinal axis 8, as illustrated in FIG. 5.

The spirally shaped tissue-receiving element 2 and the edge 9 of said cylindrical element 4 are cooperating with each other in such a manner that, as will be explained further, a cutting function can be obtained when taking a tissue sample. To this aim, the cylindrical element 4 fits precisely around the tissue-receiving element 2. In order to still improve the cutting function, the edge 9 of said cylindrical element 4 is made as a cutting edge.

Hereby, the edge 9 preferably shows several cutting edge portions, in this case, two, 10 and 11, respectively, which show an inclination A which is different from the inclination B of the body 7 of the spirally shaped tissue-receiving element 2, and whereby preferably the inclination A even is opposed to the inclination B.

As explained in the introduction, the whole unit may be made as a biopsy needle, as well as a catheter. In the first case, the whole then shows a limited length, and the cylindrical element 4 is made as a rigid or relatively rigid body, whereas in the second case, the cylindrical element 4 then consists of a supple, relatively pliable cylindrical guide, which thus mostly is considerably longer than in the case of a biopsy needle.

The device 1 of the invention can be operated manually as well as by means of an appropriate apparatus. An example of such apparatus 12 is illustrated schematically in FIG. 6. This apparatus 12 substantially consists of a manual instrument with a housing 13 and driving means 14 provided therein for operating, driving, respectively, the tissue-receiving element 2 and the cylindrical element 4.

The driving means 14 comprise, on one hand, a manual driving mechanism 15 for axially shifting, as well as rotating, the spirally shaped tissue-receiving element 2 and, on the other hand, a motorized driving mechanism 16 for the cylindrical element 4.

The driving mechanism 15 comprises an operation button 17 to which said portion 3 can be coupled, by means of the extremity 18 of this portion 3, which is situated opposed to the extremity 19 where the tissue-receiving element 2 is attached to the portion 3. In FIG. 6, this is obtained by means of a schematically represented clamping coupling 20. It is, however, clear that a variety of coupling systems can be applied to this end.

The operation button 17 allows for the portion 3, which is attached thereto, to be shifted, as well as turned, in longitudinal direction.

The driving mechanism 16 comprises a rotatable portion 21, the rotational movement of which can be transferred to the cylindrical element 4 by means of a coupling 22. In the represented example, this is a simple clamping coupling, whereby the cylindrical element 4 is clamped into the portion 21 at its upper end. Of course, other forms of couplings are possible. The portion 21 can rotate and can be shifted axially along the spirally shaped tissue-receiving element. For the rotation, this latter, by means of a gearwheel transmission 23, is in connection with an electric motor 24, which, for example, can be fed by means of a battery 25 and can be activated by means of an operation element 26, such as a pressure button or such.

Hereby, the gearwheel 27 represented in FIG. 6 axially is mounted in a fixed position, however, the portion 21 driven rotatingly by this gearwheel is axially shiftable in respect to said gearwheel 27.

Apart therefrom, the driving mechanism 16 also comprises a movement mechanism 28 for shifting the cylindrical element 4 in axial direction. This movement mechanism 28 in this case is formed by a pressure button 29 which, by means of a lever mechanism 30, is in connection with the portion 21, such that the movement of the pressure button 29 results in the axial shifting of the portion 21 and the cylindrical element 4 attached therein.

The functioning of the device 1, as well as the use of said apparatus 12, is explained hereafter by means of FIGS. 7 to 16.

Figure 8:
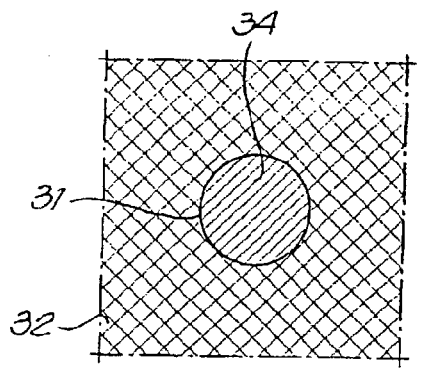

Apart from the use of said tissue-receiving element 2 and the cylindrical element 4, in the represented example also the classical localization needle 31 is used, or, in the case of catheters, a localization wire. As represented in FIGS. 7 and 8, this localization needle 31 first is pushed into the tissue 32 and brought with its tip 33 up to the location where one wants to take a tissue sample. Positioning hereby may take place by means of a permanent radiological representation of the penetration of the localization needle 31 in the tissue 32, more particularly by thereby permanently scanning the body part concerned.

Figure 9:
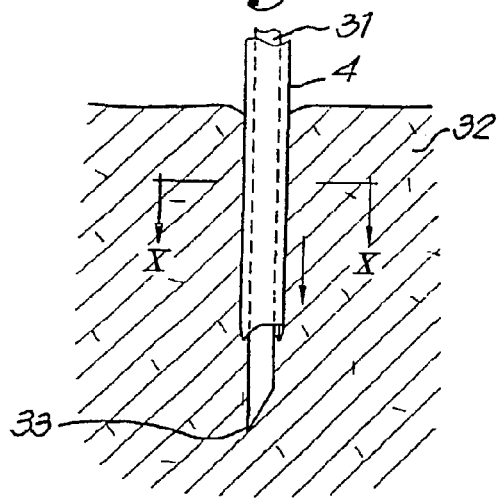
Figure 10:
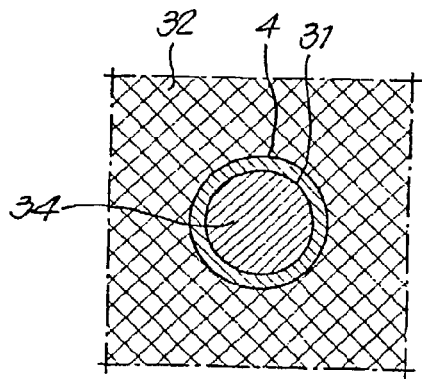
Figure 11:
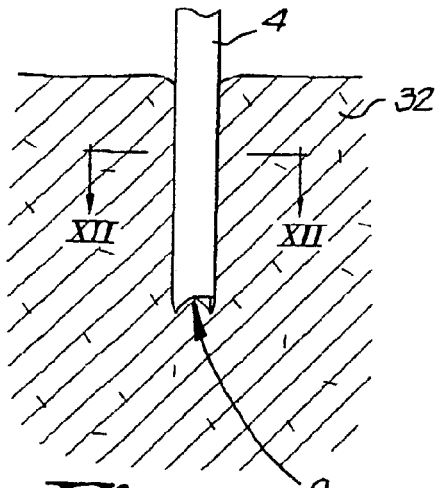
Figure 12:
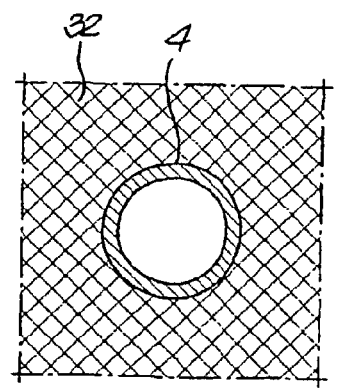
Figure 13:
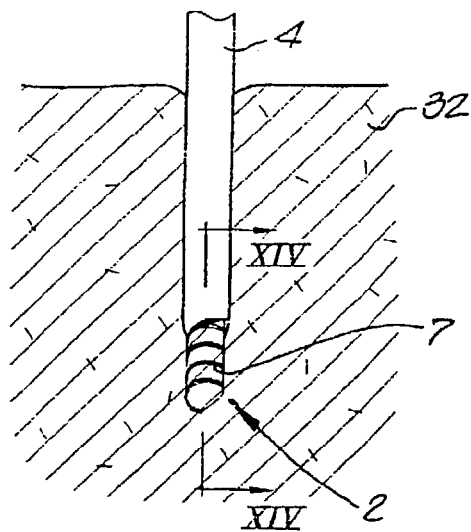
Figure 14:
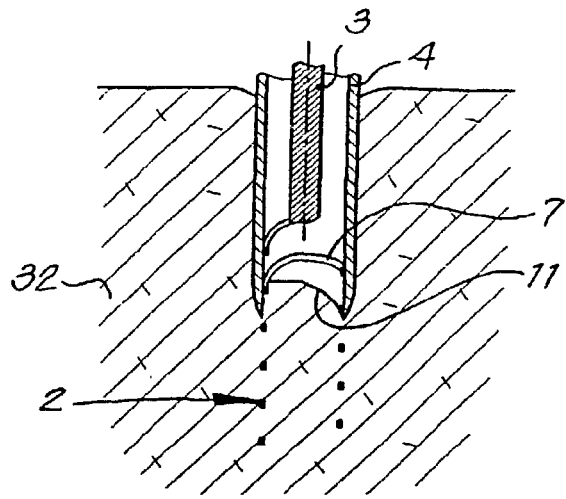

When the tip 33 of the localization needle 31 is situated at the location where the tissue sample must be taken, the cylindrical element 4, as illustrated in FIGS. 9 and 10, is slid over the localization needle 31 up to the tip 33. Subsequently, the localization needle 31 is pulled back and removed, as a consequence of which a condition is obtained as illustrated in FIGS. 11 and 12. Alternatively, the spirally shaped tissue-receiving element 2 can be slid over the localization needle or wire and thereover the cutting cannula or, thus, the element 4, or, as explained in the following, the cutting catheter.

In a following step, the spirally shaped tissue-receiving element 2 is slid through the cylindrical element 4 until it comes into contact with the tissue 32. Alternatively, the spirally shaped tissue-receiving element 2 can penetrate the tissue, after which the cylindrical element follows.

Subsequently, the spirally shaped tissue element 2 is screwed into the tissue 32 by means of a turning movement. This screwing-in is performed manually, either directly by turning at the bar- or wire-shaped portion 3, or indirectly, by first placing the apparatus 12 onto the cylindrical element 4 and said portion 3, whereby the turning then is realized by means of the operation button 17. Finally, a condition is obtained as represented in the cross-section of FIG. 14.

In a following step, the cylindrical element 4 is moved downward over the tissue-receiving element 2, preferably in conjunction with a relatively fast turning movement, preferably in reversed rotational direction in respect to the spiral. Hereby, the cutting edge portions 10–11 form a cylindrical cut, this being obtained, amongst others, by the cooperation between these cutting edge portions 10–11 and the spirally shaped tissue-receiving element 2.

The turning movement of the cylindrical element 4 can be obtained by means of the motor 24, which can be switched on by means of the operation element 26. The simultaneous axial displacement of the cylindrical element 4 over the spirally shaped tissue-receiving element 2 is realized by pushing in the push-button 29.

Figure 15:
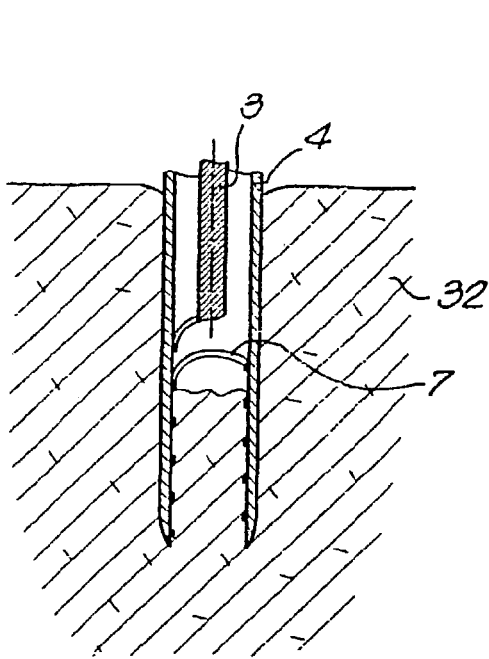
Figure 16:
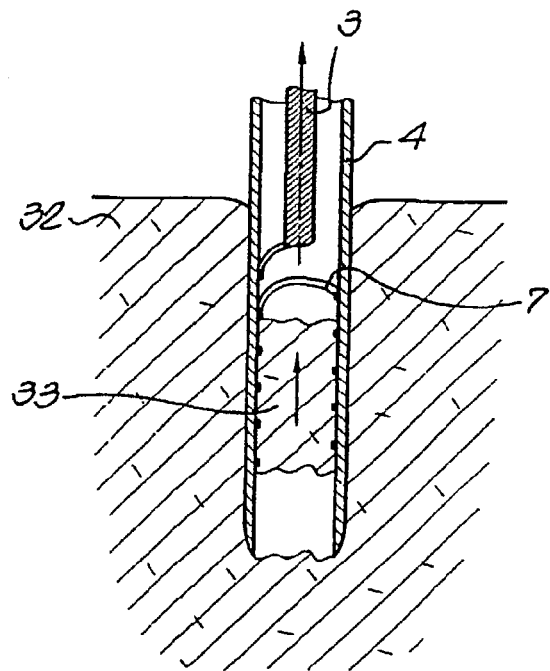

The cylindrical element 4 is displaced over a distance which coincides or almost coincides with the axial length of the tissue-receiving element 2, which results in a condition as represented in FIG. 15. By subsequently drawing back the tissue-receiving element 2 by exerting a traction force onto said portion 3, the tissue portion taken up in the spirally shaped tissue-receiving element 2 is pulled loose, as a result of which, as illustrated in FIG. 16, a tissue sample 34 is obtained which, together with the tissue-receiving element 2 and the cylindrical element 4, can be removed from the tissue 32.

It is noted that variants to the method described heretofore are possible, whereby either additional accessories can be used or not. Acording to a not-represented variant, for example, use can be made of an additional cylindrical element which does not comprise a cutting edge, whereby the method for taking a tissue sample then substantially consists in, successively, providing the localization needle 31, sliding said additional cylindrical element over the localization needle 31, drawing back the localization needle 31, sliding the tissue-receiving element 2 through said additional cylindrical element, screwing the tissue-receiving element 2 into the tissue 32, drawing back the additional cylindrical element, providing the cylindrical element 4, which, as aforementioned, is provided with a cutting edge, over said portion 3, performing a cylindrical cut by means of the cylindrical element 4, and pulling off and removing the tissue sample 34 thus present in the tissue-receiving element 2.

It is also clear that an apparatus 12 does not necessarily have to be used. So, for example, all operations can be realized manually.

In the forms of embodiment described heretofore, the cylindrical element 4 is made as a hollow needle, more particularly a biopsy needle, in other words, as an element which is relatively rigid. According to an important variant of the invention, the whole unit, instead of being integrated into a biopsy needle, realized as a biopsy needle, respectively, is realized as a catheter.

Figure 17:
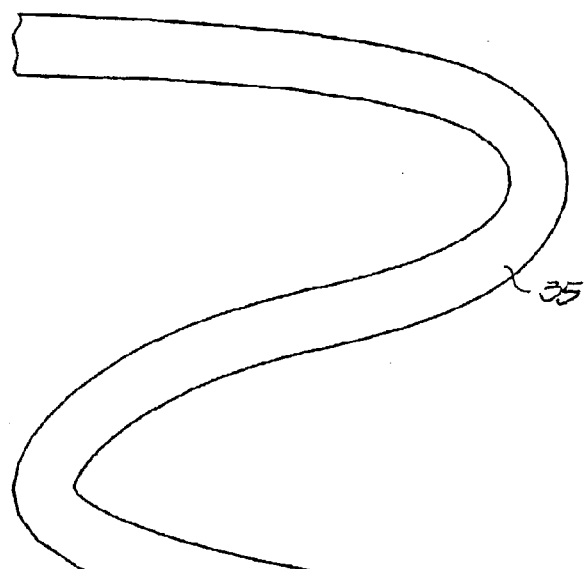
FIG. 17 represents a variant of the invention.
Figure 18:
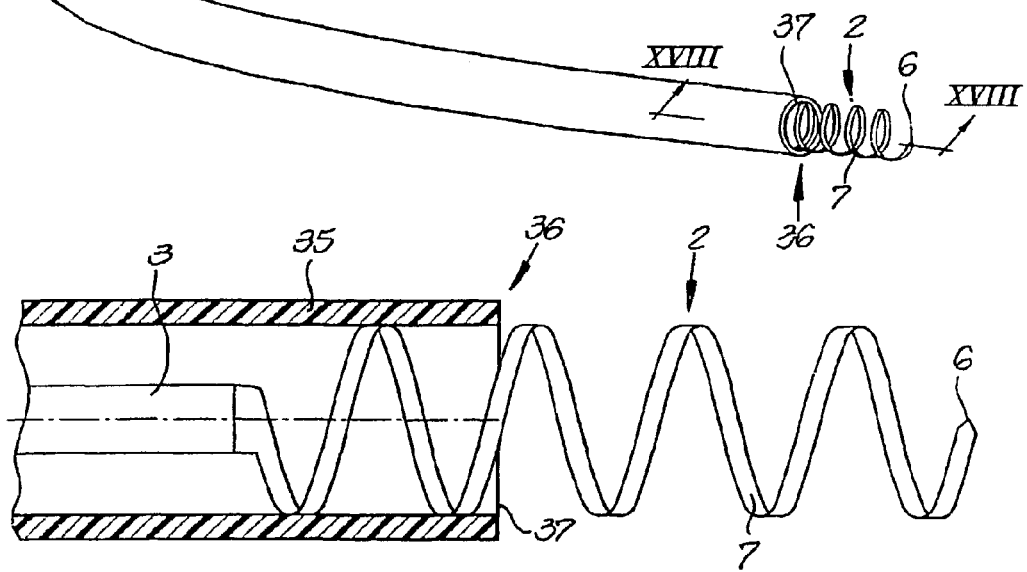
FIG. 18 schematically and at a larger scale represents a cross-section according to line XVIII—XVIII in FIG. 17.

A first example thereof is represented in FIGS. 17 and 18. The catheter 35, which then fulfills the function of cylindrical element 4, is made in a known manner of a supple material. Said spirally shaped tissue-receiving element 2 can be moved through the catheter 35, or anyhow can be moved axially at least over a well-defined length, such that, at the free extremity 36 of the catheter 35, it can be brought into a tissue portion which is situated in front of the end of the catheter 35.

In the represented example of FIGS. 17 and 18, the catheter 35 has a blunt edge 37.which possibly also can be rounded off. According to a not-represented variant, the edge 37 can also be realized as a cutting edge.

Figure 19:
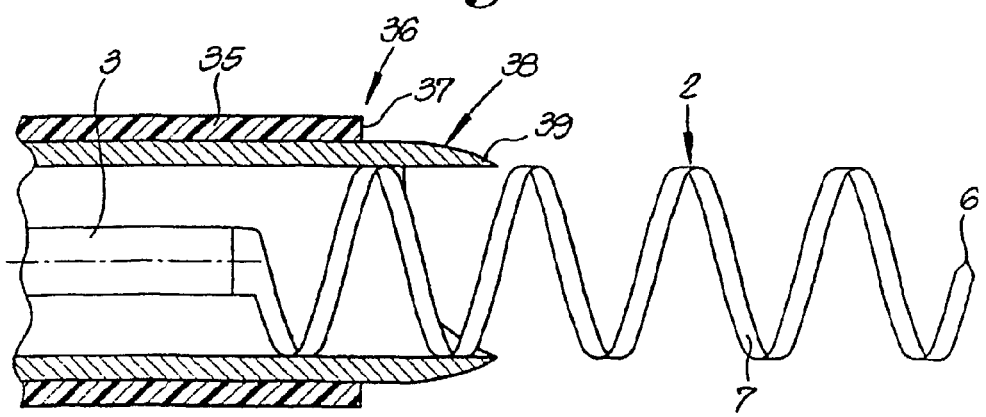
FIG. 19 represents a variant for a view analogous to that of FIG. 18.

In FIG. 19, a second example is represented, whereby two cylindrical elements are applied, on one hand, the actual catheter 35 and, on the other hand, an element 38 which is movable therein and preferably also turnable and which is provided with a cutting edge 39. During the providing and positioning of the catheter 35, the spirally shaped tissue-receiving element 2 and the element 38 then are drawn into said catheter, such that they can not cause any damage during these operations. Only after the catheter 35 is situated with its extremity 36 next to the tissue portion from which a tissue sample 34 must be taken, the tissue-receiving element 2 and said element 38 are presented outside of the extremity 36. Hereby, one may operate in a manner analogous to the one described by means of the FIGS. 14 to 16, however, with the difference that the spirally shaped tissue-receiving element 2 is brought up to the surface of a tissue and subsequently is screwed into the surface, whereas the catheter 35 in fact remains outside of the actual tissue.

According to a particular form of embodiment of the invention, the spirally shaped tissue-receiving element 2 is manufactured of a springy material, whereby it is deformable between at least two positions, on one hand, a free position whereby it takes the shape of a spiral, and, on the other hand, a deformed position, whereby it is in a condition in which it is flattened, elongated, respectively, to a minor or major extent. An example thereof is represented in the FIGS. 20 to 22, such in combination with a cylindrical element in the form of a catheter 35. Hereby, the tissue-receiving element 2 can be slid in, out, respectively, of the cylindrical element, in this case, the catheter 35. In the slid-in condition, which is illustrated in FIG. 20, the body 7 of the spirally shaped tissue-receiving element 2 enforcedly is in elongated condition, as the small diameter of the catheter 35 does not allow that the body 7 extends spirally therein. When the tissue-receiving element 2 is slid out, it again takes up a spiral condition, as represented in FIGS. 21 and 22, respectively.

This allows for that the tissue-receiving element 2, in the condition of FIG. 20, can easily, without any hooking, be brought into the proximity of a tissue portion 40, from which a tissue sample must be taken, and only thereafter can be brought into the spirally shaped usage condition of FIG. 22. Subsequently, this tissue-receiving element 2 can be screwed into the tissue portion 40, after which, due to the drawing-back, a tissue sample will be pulled loose. This tissue sample then can easily be removed from the patient's body by removing the catheter 35 from the body, with the tissue-receiving element 2 in the condition of FIG. 22.

In FIGS. 23 and 24, a variant is represented, whereby the device 1, apart from said spirally shaped tissue-receiving element 2, comprises at least one additional spirally shaped element 41, which can cooperate with the spirally shaped tissue-element 2, more particularly, is turnable around this latter. Due to the mutual turning, analogous as with said cylindrical element 4, a cylindrical cut around a tissue sample can be realized.

Preferably, both spirally shaped elements, 2 and 41, respectively, consist of a springy material and are deformable between a free spiral condition and an elongated, more flattened condition, in such a manner that they both can be drawn into an oblong holder 42, analogous as explained by means of FIGS. 20 to 22. In the embodiment of FIGS. 23 and 24, the holder 42 is realized in several parts and consists of an inner guide 43 for the tissue-receiving element 2 and an outer guide 44 for the additional spirally shaped element 41.

The present invention is in no way limited to the forms of embodiment described as an example and represented in the figures, on the contrary may such device be realized in different forms and dimensions, without leaving the scope of the invention.

So, for example, is it not excluded to apply surrounding cutting elements which are realized different than the cylindrical element 4 represented in FIG. 1.

Further, it must be emphasized that the invention, inasmuch as it relates to catheters, is not limited to spirally shaped tissue-receiving elements, but that it also relates to embodiments whereby other tissue-receiving elements, of any design, are applied in combination with a catheter, whereby between the actual tissue-receiving element and the catheter possibly other additional elements, for example, cutting elements, can be present. This inventive concept, for example, also contains the possibility that a catheter can be equipped with a tissue-receiving element at its extremity, such as described in U.S. Pat. No. 6,027,458, under the condition that this then is realized sufficiently short and/or sufficiently supple in order to be able to follow all movements of the catheter.

Figure 25:
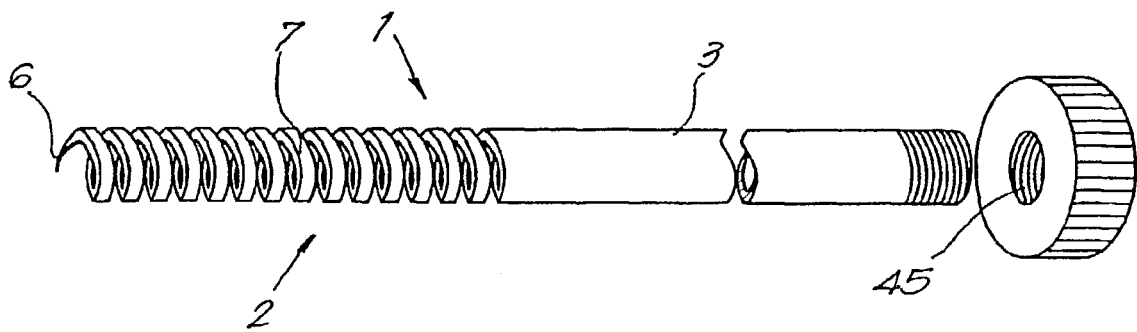
FIG. 25 represents another tissue-receiving element according to the invention.

Finally, FIG. 25 represents a practical example of a tissue-receiving element 2 which is realized according to the invention and which is suitable for taking tissue samples from breast tissue. This element 2 is formed of a hollow needle with, for example, an inner diameter of 2 mm and an outer diameter of 3 mm. The actual helix extends over an axial length of approximately 3 cm. At the end of portion 3, a cylindrical turning button 45 can be provided, for example, screwed thereon.

Figure 26:
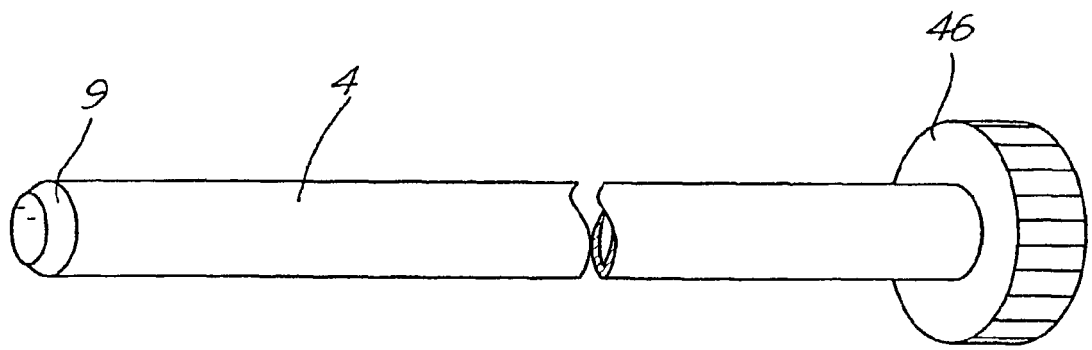
FIG. 26 represents a cylindrical element which can cooperate with the tissue-receiving element of FIG. 25.

FIG. 26 shows a pertaining cylindrical element 4, with then, for example, an inner diameter of 3 mm and an outer diameter of 5 mm. The edge 9 is made conical, and at the manipulator end, also a turning button 46 is provided.

Figure 27:
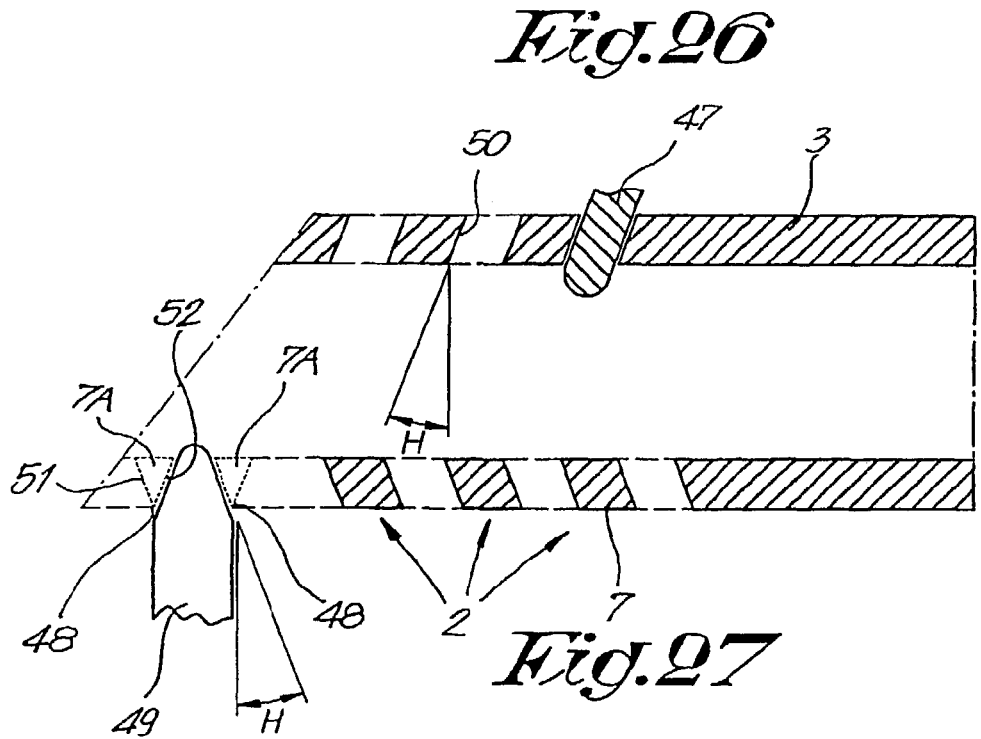
FIG. 27 schematically represents how the tissue-receiving element of FIG. 25 can be manufactured.
Figure 31:
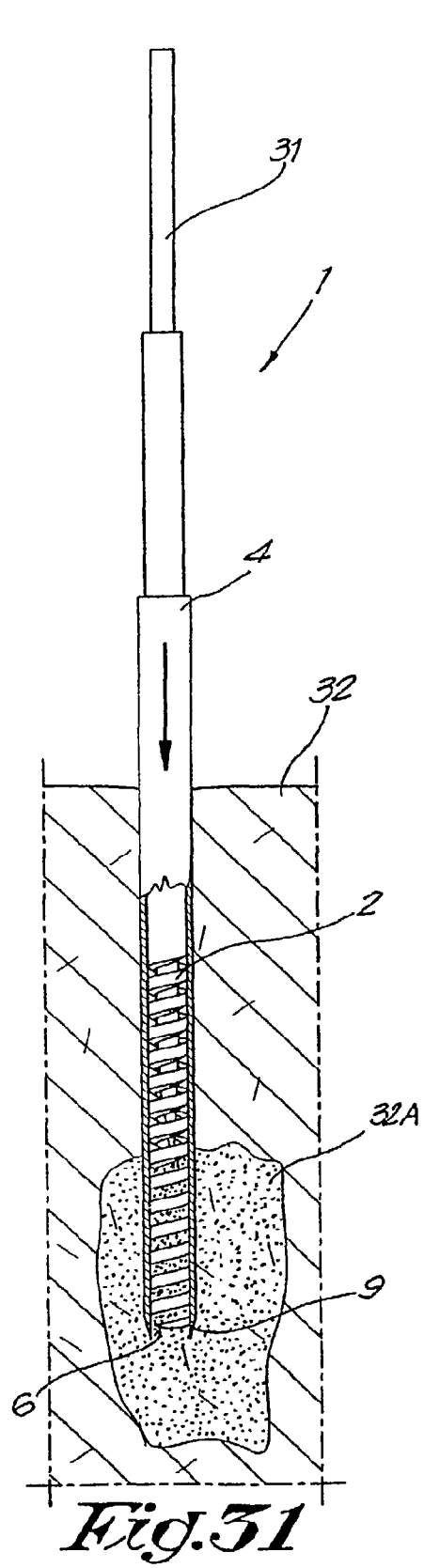

FIG. 27 represents an example of a technique for realizing the tissue-receiving element 2 of FIG. 25. Hereby, one starts from a tube-shaped element and, by means of a cutting instrument, such as a milling element or mill cutter 47, a helical cut in a portion thereof is realized. The remaining part then forms the spirally shaped tissue-receiving element.

Of course, the body 7 can be created with different forms of cross-sections. At the left in FIG. 27, an alternative form of embodiment for the body is shown in dashed line, this form being indicated by 7A, which has a cross-section with a shape which tapers towards the outside, and preferably ends in a tip 48. This form can be realized by using a cutting tool 49 having a shape as shown in FIG. 27.

As further indicated in FIG. 27, when the body 7-7A has inclined lateral surfaces 50-51-52, in general it is preferred that these lateral surfaces have an inclination H in respect to the plane perpendicular to the axial direction of the device, which is less than 30 degrees, and preferably is zero.

In FIGS. 28 to 32, it is shown how a device 1 according to the invention can be used, which device 1 comprises a tissue-receiving element 2 similar to the one shown in FIG. 25, a cylindrical element 4 similar to the one shown in FIG. 26, and further a localization needle 31 which axially can be shifted through the tissue-receiving element 2.

FIG. 28 shows how the localization needle 31 is pushed into the tissue 32 and brought with its tip 33 up to the location of the tissue portion 32A from which a sample has to be taken. As mentioned before, this can be done under permanent radiological control.

In the next step, the tissue-receiving element 2, together with the cylindrical element 4 therearound, is slid over the localization needle 31 up into the position as represented in FIG. 29. From that moment on, the localization needle 31 can possibly be retracted, although this is not really necessary.

Subsequently, as shown in FIG. 30, the spirally shaped tissue-receiving element 2 is screwed into the tissue portion 32A. Then, the cylindrical element 4, the front edge of which acts as a knife, is slid over the tissue-receiving element 2, whereby this cylindrical element 4 preferably also will be rotated to enhance the cutting action. Hereby, it should be noted that the cutting action also is enhanced due to the cooperation between the edge of cylindrical element 4 and the windings of the spirally shaped tissue-receiving element 2, which in fact results in a sort of cutting action similar to a cutting action obtained by scissors.

As a result of said cutting action, the tissue taken up in the tissue-receiving element 2, is cut off along the cylindrical surface defined by the outer side of the tissue-receiving element 2, resulting in that at the end of the cutting action, the sample taken up in the tissue-receiving element 2 only remains attached to the rest of the tissue portion 32A at one axial end.

Figure 32:
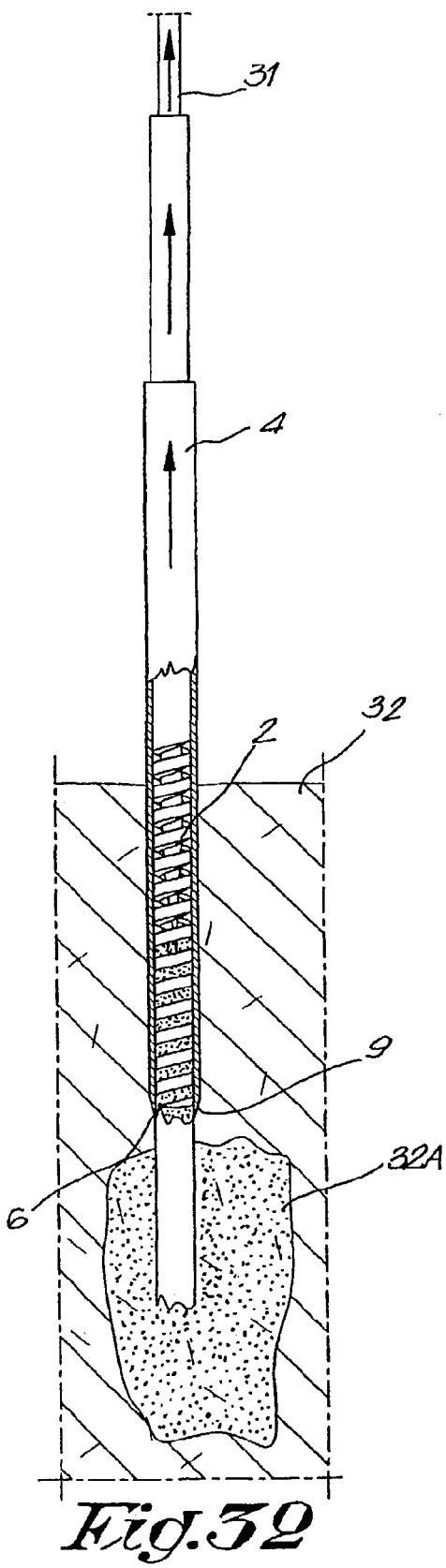

Finally, as shown in FIG. 32, the complete device 1 is retracted. As the sample is firmly anchored within the tissue-receiving element 2, the sample is caused to be withdrawn together with the device 1, during which action the small connection with the remaining tissue portion 32A is broken. Finally, after having completely retracted the device 1, the sample can be taken out of the device 1.

The invention claimed is:

1. A device for taking a tissue sample comprising a spirally shaped tissue-receiving element having a non-round cross-section and having an outer free extremity extending in and pointing in a direction along a prolongation of a spiral course of the spirally shaped tissue-receiving element to form a penetrating instrument, and a cutting element cooperating with the spirally shaped tissue-receiving element, in conjunction with a circumference of the spirally shaped tissue-receiving element for providing a cutting function.

2. The device of claim 1, wherein the spirally shaped tissue-receiving element comprises one or a combination of two or more of following features:

the spirally shaped tissue-receiving element has a helical course;
the spirally shaped tissue-receiving element surrounds a free axial passage space;
a spiral of the spirally shaped tissue-receiving element, in a direction perpendicular to an axial direction, has a width smaller than one third of a global diameter taken by the spirally shaped tissue-receiving element;
the spirally shaped tissue-receiving element extends over several turns;
the spirally shaped tissue-receiving element has a sharp point at a free front extremity;
the sharp point at the free front extremity extends in the direction along the prolongation of the spiral course of the spirally shaped tissue-receiving element;
the spirally shaped tissue-receiving element has a body with a flat cross-section;
the spirally shaped tissue-receiving element has a body having a cross-section tapering towards an outside;
the spirally shaped tissue-receiving element has a body with lateral surfaces having an inclination of less than about 30 degrees with respect to a plane perpendicular to an axial direction of the device.

3. The device of claim 2, wherein the body having the tapering cross-section tapering towards the outside ends in a tip.

4. The device of claim 1, wherein the spirally shaped tissue-receiving element is located at an end of a shaped portion.

5. The device of claim 4, wherein the shaped portion has a shape selected from the group consisting of oblong shape, bar-shape, wire-shape, and combinations thereof.

6. The device of claim 1, further comprising at least one cylindrical element surrounding the spirally shaped tissue-receiving element.

7. The device of claim 6, wherein the cylindrical element forms the cutting element, and wherein the spirally shaped tissue-receiving element and an edge of the cylindrical element mutually cooperate for creating the cutting function.

8. The device of claim 7, wherein the cutting function is created by a mutual rotational and/or axial movement of the spirally shaped tissue-receiving element and the cylindrical element.

9. The device of claim 8, wherein the front edge of the cylindrical element forms a cutting edge.

10. The device of claim 9, wherein an inclination of the cutting edge is opposed to an inclination of the spirally shaped tissue-receiving element.

11. The device of claim 9, wherein an inclination of one or more portions of the cutting edge is opposed to an inclination of the spirally shaped tissue-receiving element.

12. The device of claim 7, wherein the spirally shaped tissue-receiving element is of a springy material deformable between at least two positions, a free position and a deformed position, wherein in the free position the spirally shaped tissue-receiving element takes shape of a spiral and in the deformed position the spirally shaped tissue-receiving element is flattened, elongated, respectively, to a minor or major extent.

13. The device of claim 12, wherein the cylindrical element is a holder for slidingly receiving one or more shaped tissue-receiving elements for moving the spirally shaped tissue-receiving element in and out of the cylindrical element, and wherein the spirally shaped tissue-receiving element is in the undeformed condition when situated in the cylindrical element.

14. The device of claim 1, further comprising at least one hollow or thread shaped spirally shaped element cooperating with the spirally shaped tissue-receiving element.

15. The device of claim 14, wherein the spirally shaped element is the cutting element extending around the spirally shaped tissue-receiving element, wherein a cutting effect is created during a mutual turning movement of the spirally shaped element and the spirally shaped tissue-receiving element.

16. The device of claim 15, further comprising a motorized driver for turning the spirally shaped element and the spirally shaped tissue-receiving element and for driving the cutting element in a rotating manner around the spirally shaped tissue-receiving element.

17. The device of claim 1, wherein the device is a biopsy needle or is adaptable for a biopsy needle.

18. The device of claim 1, wherein the device is a flexible catheter or is adaptable for a catheter.

19. The device of claim 1, further comprising a localization element axially movable in the spirally shaped tissue-receiving element.

20. The device of claim 19, wherein the localization element is a localization needle.

21. A device for taking a tissue sample comprising a flexible catheter and the spirally shaped tissue-receiving element of claim 18 cooperating with the flexible catheter.

22. The device of claim 21, wherein the spirally shaped tissue-receiving element is displaceable with respect to the catheter between at least two positions, wherein in one position the tissue-receiving element is situated at least partially outside a front end of the catheter and in another position the tissue-receiving element is situated in a drawn-in position in the catheter.

* * * * *